United States Patent [19]

Chaen et al.

[11] Patent Number: 5,916,371
[45] Date of Patent: Jun. 29, 1999

[54] CRYSTALLINE POWDERY SACCSHARIDE, ITS PREPARATION AND USES

[75] Inventors: Hiroto Chaen; Kazuhisa Mukai; Toshio Miyake, all of Okayama, Japan

[73] Assignee: Kabushiki Kaisha Hayashibara Seibutsu Kagaku Kenkyujo, Okayama, Japan

[21] Appl. No.: 08/985,349

[22] Filed: Dec. 4, 1997

[30] Foreign Application Priority Data

Dec. 10, 1996 [JP] Japan ................................. 8-344511

[51] Int. Cl.⁶ .................................. C13F 1/02; C13F 3/00
[52] U.S. Cl. ................................ 127/29; 127/58; 127/60; 127/61
[58] Field of Search .................... 127/29, 58, 60, 127/61

[56] References Cited

U.S. PATENT DOCUMENTS 5,441,644  8/1995  Kinouchi ............................. 210/651

FOREIGN PATENT DOCUMENTS

| | | |
|---|---|---|
| 0447125 | 9/1991 | European Pat. Off. . |
| 0628630 | 12/1994 | European Pat. Off. . |
| 0636632 | 2/1995 | European Pat. Off. . |
| 0636693 | 2/1995 | European Pat. Off. . |
| 0670326 | 9/1995 | European Pat. Off. . |
| 0690130 | 1/1996 | European Pat. Off. . |
| 0707062 | 4/1996 | European Pat. Off. . |
| 0739983 | 10/1996 | European Pat. Off. . |
| 8216695 | 12/1983 | Japan . |
| 4281795 | 10/1992 | Japan . |
| 7170977 | 7/1995 | Japan . |
| 7213283 | 8/1995 | Japan . |
| 873482 | 3/1996 | Japan . |
| 8131182 | 5/1996 | Japan . |

OTHER PUBLICATIONS

W. Ruland, "X–Ray Determination of Crystallinity and Diffuse Disorder Scattering", Acta Cryst., vol. 14 pp. 1180–1185, (Jan. 11, 1961).

*Primary Examiner*—David Brunsman
*Attorney, Agent, or Firm*—Browdy and Neimark

[57] ABSTRACT

A stable crystalline powdery saccharide having a crystallinity of 40% or more, less hygroscopicity, satisfactory fluidity, and beneficial handleability, which is obtainable from an aqueous solution, containing trehalose and a different saccharide(s) crystallizable in the presence of trehalose, by crystallizing the trehalose along with the different saccharide(s).

14 Claims, 3 Drawing Sheets

CRYSTALLINE POWDERY SACCSHARIDE, ITS PREPARATION AND USES

BACKGROUND OF THE INVENTION

1. Field of the Invention

The present invention relates to a crystalline powdery saccharide, its preparation and uses, more particularly, to a crystalline powdery saccharide obtained by crystallizing trehalose along with a different saccharide(s) crystallizable in the presence of trehalose, its preparation and uses in food products, cosmetics, and pharmaceuticals.

2. Description of the Prior Art

Trehalose, as disclosed in Japanese Patent Kokai No.213, 283/95, can be directly produced from starch by contacting reducing partial starch hydrolysates, having glucose polymerization degrees of 3 or more and being obtained from starch as a material, with both a non-reducing saccharide-forming enzyme that forms non-reducing saccharides having a trehalose structure as an end unit, and a trehalose-releasing enzyme that releases the trehalose structure from such non-reducing saccharides. Conventional methods for producing trehalose from maltose as a material include, for example, a method using a maltose/trehalose converting enzyme as disclosed in Japanese Patent Kokai No. 170,977/95, and a method using maltose- and trehalose-phosphorylases as disclosed in Japanese Patent Kokai Nos. 216,695/83 and 131,182/96. These methods, however, are not yet perfect on the trehalose yield; the trehalose yield to the material starch and/or maltose is at most 50–90 w/w %, on a dry solid basis (d.s.b.), (throughout the present specification, the wording "w/w %" is abbreviated as "%", unless specified otherwise), and the produced trehalose usually contains glucose, maltose, maltotriose, maltotetraose, etc., as coexisting saccharides.

As disclosed in Japanese Patent Kokai Nos. 213,283/95 and 170,977/95, it is known that trehalose is relatively-easily crystallized but the coexisting saccharides are deemed to be hardly crystallizable because trehalose has a crystallization inhibitory activity to the saccharides. Therefore, in the trehalose production, high trehalose content solutions produced from starch and/or maltose are usually decolored and desalted for purification, and concentrated, followed by crystallizing trehalose by adding a trehalose seed to the concentrate, separating the resultant mixture to remove impurities, and collecting crystalline trehalose hydrate with a relatively-high purity. It was found, however, that powdery saccharides containing crystalline trehalose hydrate and coexisting saccharides have serious demerits that they easily adsorb moisture to be solidified and easily lose their fluidity or free-flowing ability.

In the case of using a separation process for removing coexisting saccharides, a relatively-high quality crystalline trehalose hydrate, with a relatively-low moisture absorbency and an extremely-high stability and handleability, can be obtained. However, molasses containing quantities of coexisting saccharides as by products are formed so that beneficial uses of the molasses have been desired. Regarding to this, the present applicant, as disclosed in European Patent Application No. 739986, had established a high trehalose content syrup, wherein the trehalose crystallization is effectively prevented, which can effectively utilize the above molasses. The use, however, is just for a convenient method. Intrinsically, highly required is to basically improve the property of powdery saccharides containing molasses comprising crystalline trehalose hydrate and coexisting saccharides, and to establish high quality powdery saccharides. It is also strongly required that a method for preparing molasses, comprising trehalose and quantities of coexisting saccharides, into stable powdery saccharides.

SUMMARY OF THE INVENTION

The object of the present invention is to establish stable crystalline powdery saccharides with less moisture absorbency, obtainable from solutions produced from starch and/or maltose comprising trehalose and a different saccharide(s) such as glucose, maltose, maltotriose, and/or maltotetraose; and to establish the preparation and uses.

To solve the above object, the present inventors took interest in the crystallinity of powdery saccharides, more particularly, energetically studied on the crystallinity of saccharides in the presence of trehalose. As a result, they unexpectedly found that, among these saccharides, particular saccharides can be crystallized along with trehalose; and crystalline powdery saccharides obtained by pulverizing the crystallized saccharide is a stable powder with less moisture absorbency. They also established the preparation and uses of the crystalline powdery saccharide in compositions. Thus, they accomplished this invention. The crystalline powdery saccharide according to the present invention is obtained by crystallizing trehalose along with a different saccharide(s) crystallizable in the presence of trehalose into a crystalline powdery saccharide comprising crystals of the trehalose and different saccharide(s).

BRIEF DESCRIPTION OF THE ACCOMPANYING DRAWINGS

DETAILED DESCRIPTION OF THE INVENTION

Figure 1:
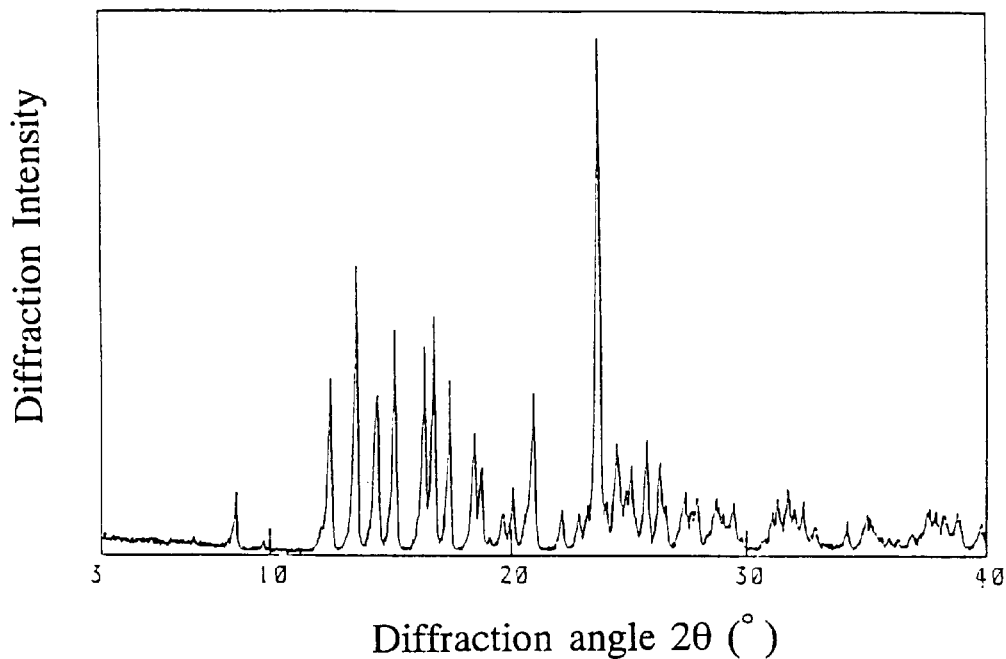
FIG. 1 is a powder x-ray diffraction pattern of trehalose as a control.

The coexisting saccharides crystallizable in the presence of trehalose according to the present invention include those derived from starch and/or maltose as materials, produced during trehalose production, and others formed by reducing or hydrogenating the above saccharides. However, the coexisting saccharides should not be restricted to those saccharides, and may be those produced by alternative methods. Particularly, glucose, maltose, sorbitol, maltitol, etc., can be suitably used, more particularly, glucose and maltose can be suitably used after crystallized into a crystalline hydrate form, while sorbitol and maltitol are suitably used after crystallized into crystalline anhydrides. The proportion of trehalose to a different saccharide(s), contained in the present crystalline powdery saccharide, is one which allows them to be crystallized, preferably, in the range of 9:1 to 1:9, d.s.b., more preferably, in the range of 8:2 to 2:8, d.s.b. It was revealed that when the present crystalline powdery saccharide has a crystallinity of about 40% or more on powder x-ray diffraction analysis, it has a lesser moisture absorbency and a satisfactory stability and handleability.

Saccharide solutions usable for producing the present crystalline powdery saccharide can be appropriately selected from the following representatives: (1) Saccharide solutions containing trehalose along with a different saccharide(s) such as glucose and maltose, which are produced from starch as a material, for example, as disclosed in Japanese Patent Kokai No. 213,283/95, by contacting starch debranching enzymes, non-reducing saccharide-forming enzymes, and trehalose-releasing enzymes with liquefied starch obtained by contacting α-amylase with starch; (2) those containing trehalose and coexisting saccharides such as glucose and maltose, which are produced from maltose as a material, for example, by contacting maltose/trehalose converting enzymes with maltose as disclosed in Japanese Patent Kokai Nos. 170,977/95, or contacting maltose- and trehalose-phosphorylases with maltose as disclosed in Japanese Patent Kokai No. 216,695/83; and (3) those containing trehalose and coexisting saccharides such as sorbitol and maltitol, which are produced from the saccharide solution of (1) or (2) by converting reducing saccharides in the saccharide solution by high-pressure hydrogenation into sugar alcohols as disclosed in Japanese Patent Kokai No. 73,482/96. The saccharide solutions thus obtained usually contain about 10–90% trehalose, d.s.b.

Any methods can be used in the present invention as long as they produce substantially non-hygroscopic powdery saccharides by crystallizing trehalose along with a different saccharide(s), which can be crystallized in the presence of trehalose, from solutions containing the trehalose and different saccharide(s), and pulverizing the mixtures. Preferably, crystalline powdery saccharides with a crystallinity of 40% or more on powder x-ray diffraction analysis, more preferably, 50% or more, can be suitably used. To produce the present crystalline powdery saccharide, pulverization methods, for example, spray drying method for massecuites, fluidized-granulation method under crystallizing conditions for saccharide solutions with a relatively-high concentration, and block-pulverization method for pulverizing crystallized and solidified massecuites into blocks can be suitably used to increase the crystallinity as much as possible. In the case of spray-drying method, massecuites, with concentrations of 65–80% and crystallinity of 5–30% for trehalose and a different saccharide(s) crystallizable in the presence of trehalose, are sprayed from nozzles using high-pressure pumps; drying the contents with air heated to temperatures that do not melt them, for example, with air heated to 60–90° C.; and blowing air heated to 30–60° C. to the contents to crystallize and age them for about 1–24 hours into saccharides with a crystallinity of 40% or more, or substantially non-hygroscopic powdery saccharides. In the block-pulverization method, the desired substantially non-hygroscopic powdery saccharides can be obtained by placing massecuites, with concentrations of 80–95% and crystallinity of 10–30% of trehalose and a different saccharide(s) crystallizable in the presence of trehalose, in vats at ambient temperature for about 1–20 days to solidity the whole contents into blocks; pulverizing the blocks by pulverization or cutting methods; and drying the pulverized saccharides with a crystallinity of about 40% or more.

Substantially non-hygroscopic powdery saccharides can be advantageously produced by concentrating in a conventional manner by heating solutions, containing trehalose and a different saccharide(s) crystallizable in the presence of trehalose, into supersaturated solutions in a melting state and with concentrations of 90% or more, mixing the supersaturated solutions with hydrous and/or anhydrous crystalline saccharides as seeds at temperatures below their melting points; finely or roughly pulverizing or shaping the contents into appropriate shapes; crystallizing the resulting products into hydrous and/or anhydrous crystalline saccharides; and ageing the resulting saccharides to give a crystallinity of about 40% or more.

As described above, the crystallization and pulverization steps in the present process can be carried out in any order or can be conducted in parallel. If necessary, these steps can be effected in a multistage manner as long as they produce the present crystalline powdery saccharide.

The present crystalline powdery saccharide thus obtained contains crystals of trehalose and a different saccharide(s). Varying to some extent depending on the degree of crystallinity, the crystalline powdery saccharide with a crystallinity of 40% or more is substantially free from hygroscopicity and solidification and has a satisfactory fluidity and handleability, and these properties greatly reduce the physical and labor costs required for the packaging, transportation, and storage.

Insubstantial hygroscopicity of the present crystalline powdery saccharide quite easily and effectively facilitates the production of powdery mixed sweeteners, solid mixed sweeteners, chocolates, chewing gums, instant juices, instant soups, granules, and tablets, which have been deemed substantially difficult to obtain.

Similarly as in the case of using conventional saccharides in an aqueous form, the present crystalline powdery saccharide has substantially the same properties of such saccharides, for example, sweetness, body-imparting ability, gloss-imparting ability, hygroscopicity, viscosity, and crystallization-preventing ability to other saccharides. These enable the present crystalline powdery saccharide to be used arbitrarily and widely in food products, cosmetics, and pharmaceuticals.

When used as a sweetener, the present crystalline powdery saccharide can be used together with one or more adequate amounts of sweeteners such as powdered syrup, glucose, maltose, isomerized sugar, sucrose, honey, maple sugar, sorbitol, xylitol, lactitol, maltitol, dihydrocharcone, stevioside, α-glycosyl stevioside, sweet substances of *Fructus Momordicae,* glycyrrhizin, L-aspartyl L-phenylalanine methyl ester, saccharin, glycine, and alanine; and/or fillers such as dextrins, starch, and lactose.

The present crystalline powdery saccharide can be mixed with an excipient, filler, adjuvant, and binder, and formed into granules, spheres, tablets, rods, plates, and cubes, prior to use.

The present crystalline powdery saccharide has a sweetness that well harmonizes with other materials having a sour-, acid-, salty-, astringent-, delicious-, and bitter-taste, and has a satisfactory acid and heat tolerance. Because of these properties, the present crystalline powdery saccharide can be favorably used in food products in general as a sweetener, taste-improving agent, and quality-improving agent.

The present crystalline powdery saccharide can be used as a sweetener, taste-imparting agent, and quality-improving agent in seasonings such as a soy sauce, powdered soy sauce, "miso", "funmatsu-miso" (a powdered miso), "moromi" (a refined sake), "hishio" (a refined soy sauce), "furikake" (a seasoned fish meal), mayonnaise, dressing, vinegar, "sanbai-zu" (a sauce of sugar, soy sauce and vinegar), "funmatsu-sushi-su" (powdered vinegar for sushi), "chuka-no-moto" (an instant mix for Chinese dish), "tent-suyu" (a sauce for Japanese deep-fat fried food), "mentsuyu" (a sauce for Japanese vermicelli), sauce, catsup, "yakinikuno-tare" (a sauce for Japanese grilled meat), curry roux, instant stew mix, instant soup mix, "dashi-no-moto" (an instant stock mix), mixed seasoning, "mirin" (a sweet sake), "shin-mirin" (a synthetic mirin), table sugar, and coffee sugar.

Also, the present crystalline powdery saccharide can be arbitrarily used as a sweetener, taste-improving agent, and quality-improving agent in "wagashi" (Japanese cakes) such as "senbei" (a rice cracker), "arare-mochi" (a rice-cake cube), "okoshi" (a millet-and-rice cake), "mochi" (a rice paste), "manju" (a bun with a bean-jam), "uiro" (a sweet rice jelly), "an" (a bean jam), "yokan" (a sweet jelly of beans), "mizu-yokan" (a soft adzuki-bean jelly), "kingyoku" (a kind of yokan), jelly, pao de Castella and "amedama" (a Japanese toffee); confectioneries such as bun, bread, biscuit, cracker, cookie, pie, pudding, butter cream, custard cream, cream puff, waffle, sponge cake, doughnut, chocolate, chewing gum, caramel, and candy; frozen desserts such as ice cream and sherbet; syrups such as "kajitsu-no-syrup-zuke" (a preserved fruit) and "korimitsu" (a sugar syrup for shaved ice); pastes such as flour paste, peanut paste, and fruit paste; processed fruits and vegetables such as jam, marmalade, "syrup-zuke" (fruit pickles), and "toka" (conserves); cereal products such as buns, noodles, cooked rice products, and synthetic meats; pickles and pickled products such as "fukujin-zuke" (red colored radish pickles), "bettara-zuke" (a kind of whole fresh radish pickles), "senmai-zuke" (a kind of sliced fresh radish pickles) and "rakkyo-zuke" (pickled shallots); premixes for pickles and pickled products such as "takuan-zuke-no-moto" (a premix for pickled radish) and "hakusai-zuke-no-moto" (a premix for fresh white rape pickles); meat products such as ham and sausage; products of fish meat such as fish ham, fish sausage, "kamaboko" (a steamed fish paste), "chikuwa" (a kind of fish paste), and "tenpura" (a Japanese deep-fat fried fish paste); "chinmi" (relish) such as "uni-no-shiokara" (salted guts of sea urchin), "ika-no-shiokara" (salted guts of squid), "su-konbu" (processed tangle), "saki-surume" (dried squid strips) and "fugu-no-mirin-boshi" (a dried mirin-seasoned swellfish); "tsukudani" (foods boiled down in soy sauce) such as those of laver, edible wild plants, dried squid, fish, and shellfish; daily dishes such as "nimame" (cooked beans), potato salad, and "konbu-maki" (a tangle e roll); milk products; canned and bottled products such as those of meat, fish meat, fruit, and vegetable; alcoholic beverages such as synthetic sake, wine and liquors; soft drinks such as coffee, cocoa, juice, carbonated beverage, sour milk beverage, and beverage containing lactic acid bacteria; premixes such as instant pudding mixes and instant hot cake mixes; and instant premixes such as instant juices, instant coffees, instant "sokuseki-shiruco" (an instant mix of adzuki-bean soup with rice cake), and instant soup mixes.

The present crystalline powdery saccharide can be also used in feeds and pet foods for animals such as domestic animals, poultry, honey bees, silk warms, and fishes to improve their taste preferences. The crystalline powdery saccharide can be arbitrary used as a taste-improving agent, flavor-imparting agent, and quality-improving agent in other products including cosmetics and pharmaceuticals in a solid, paste, and liquid form such as a tobacco, cigarette, dentifrice, lipstick, rouge, lip cream, internal medicine, tablet, troche, cod liver oil in the form of drop, cachou, oral refrigerant, and gargle.

The present crystalline powdery saccharide can be mixed with vitamins, antibiotics, and lactic acid bacteria, and the mixtures can be arbitrarily used in a variety of fields after shaped into appropriate shapes, for example, by granulating or tabletting the mixtures with granule-shaping machines or tabletting machines.

Methods to incorporate the present crystalline powdery saccharide into the above-mentioned compositions such as food products, tobaccos, cigarettes, feeds, pet foods, cosmetics, and pharmaceuticals include those which can incorporate the crystalline powdery saccharide into such compositions before completion of their processings in an amount of 0.1% or more, preferably, 0.5% or more. For example, conventional methods such as mixing, kneading, dissolving, melting, soaking, permeating, sprinkling, applying, coating, spraying, injecting, crystallizing, and solidifying can be appropriately chosen.

The following experiments explain the present invention in more detail:

Experiment 1

Screening of saccharides crystallizable in the presence of trehalose and the influence of crystallized saccharides on the property of powdery saccharides Trehalose was dissolved and coexisted in water along with a different saccharide that can be produced as by-products during the preparation of trehalose from starch and/or maltose as materials, and the solution was studied on whether the different saccharide was crystallized along with trehalose in the presence of trehalose, and studied on the influence of the crystallization of a different saccharide on the property of hygroscopicity, solidification, and fluidity of the powdery saccharides produced. The saccharides used were commercially available preparations in a reagent grade. Powdery saccharides were prepared by adding to a 50% aqueous trehalose solution a saccharide selected from the group consisting of glucose, maltose, isomaltose, maltotriose, maltotetraose, sorbitol, maltitol, isomaltitol, maltotriitol, and maltotetraitol, in an equal amount of the trehalose, d.s.b., dissolving by heating the saccharide in the aqueous trehalose solution, and concentrating the resulting saccharide solution under a reduced pressure to give a concentration of about 80%. The concentrate was then placed in a polyethylene vat, allowed to stand at a relative humidity of about 50% and at 25° C. for 20 days, and pulverized to obtain a powdery saccharide. Using "GEI-GERFLEX RAD-IIB", a powder x-ray diffraction analyzer using CuKα ray, commercialized by Rigakudenki Co., Ltd., Tokyo, Japan, the crystallinity of each powdery saccharide was determined by the Ruland method based on powder x-ray diffraction patterns as disclosed in "Acta Crystallographica", Vol. 14, page 1,180 (1961). Representatives of powder x-ray diffraction patterns of these powdery saccharides were in FIGS. 1 to 6. These saccharides were placed in aluminum containers and allowed to stand at 25° C. for four days under a relative humidity of 90% to observe on their degrees of hygroscopicity, i.e., weight increase, whether their fluidity were passable or not, and whether they solidified or not. The fluidity was evaluated based on the three grades of "satisfactory", "passable", and "impassable" about the fluidity of the powdery saccharides in the aluminum containers when the containers were slanted, the grade "satisfactory" meant that the powdery saccharides easily slid down without resistance, the grade "passable" meant that the saccharides had a passable fluidity with some resistance, and the grade "impassable" meant that the saccharides solidified to lose fluidity. The data was in Table 1:

TABLE 1

Figure 2:
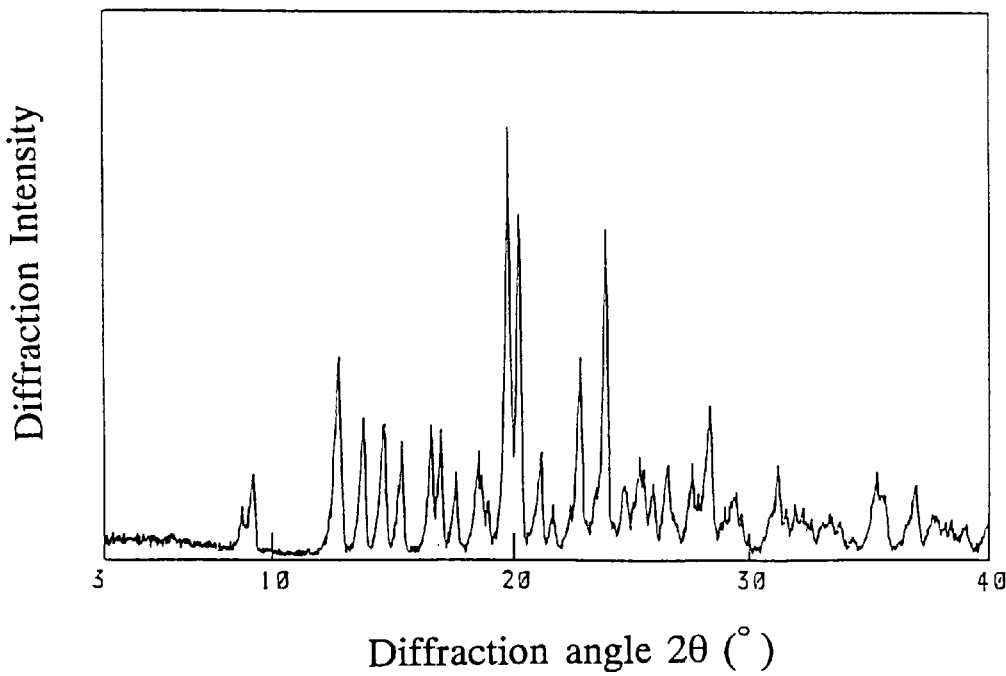
FIG. 2 is a powder x-ray diffraction pattern of trehalose containing glucose as a different saccharide.
Figure 3:
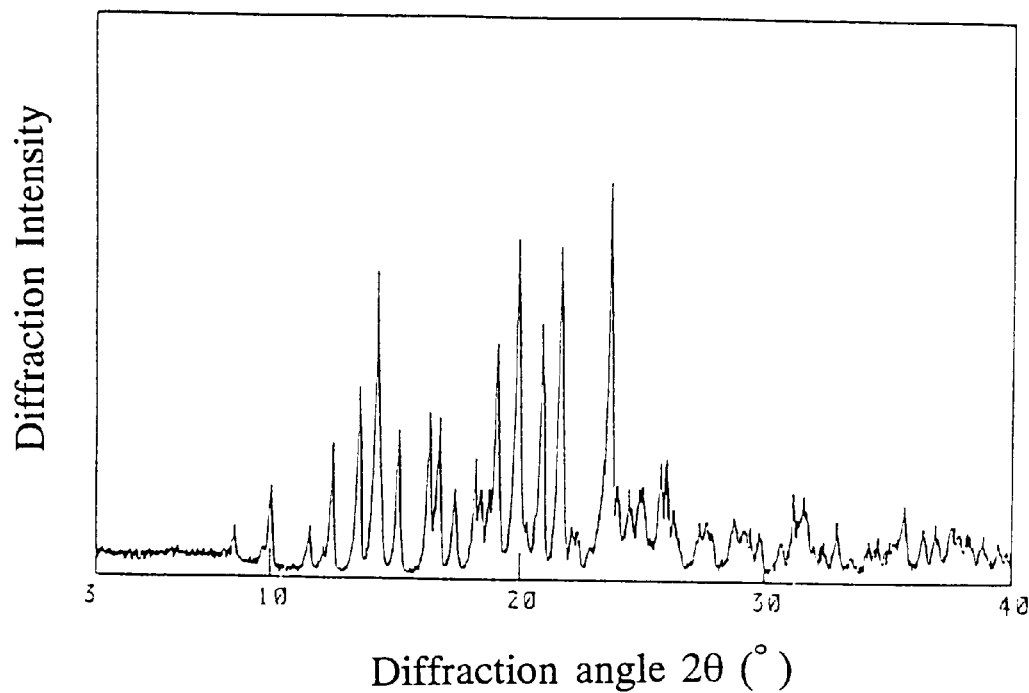
FIG. 3 is a powder x-ray diffraction pattern of trehalose containing maltose as a different saccharide.
Figure 4:
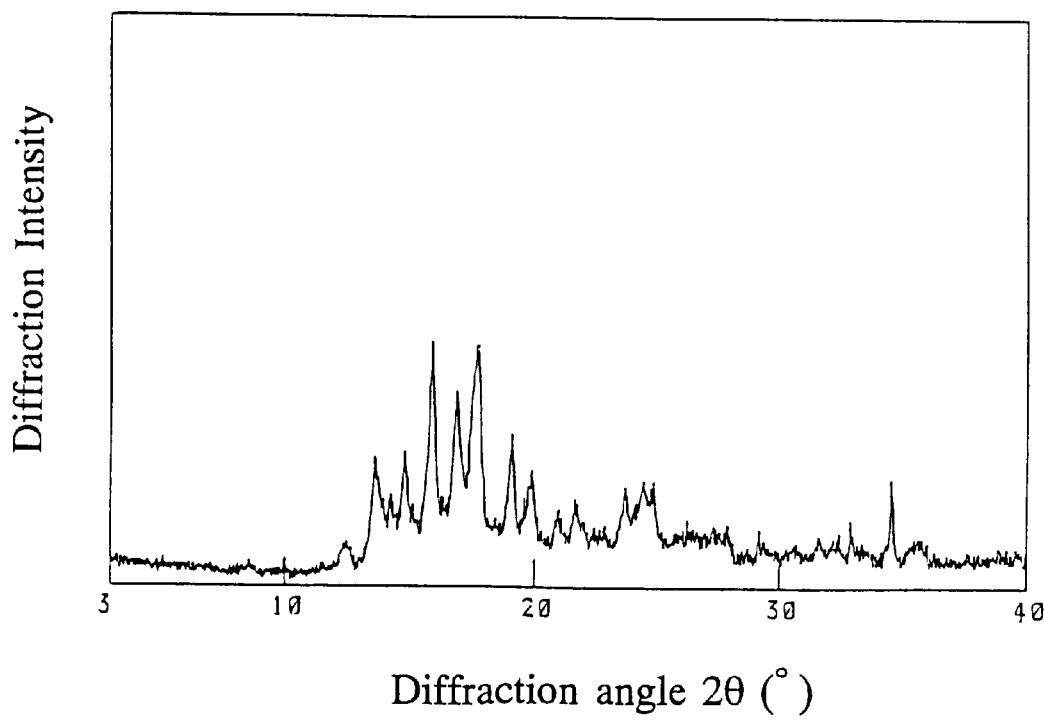
FIG. 4 is a powder x-ray diffraction pattern of trehalose containing isomaltose as a different saccharide.
Figure 5:
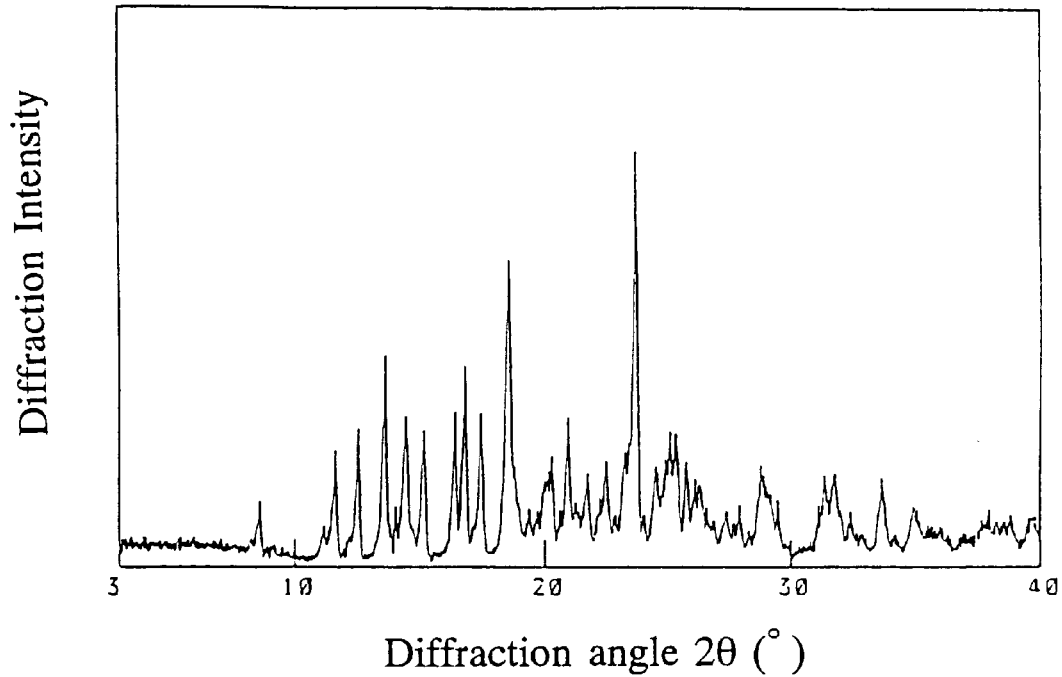
FIG. 5 is a powder x-ray diffraction pattern of trehalose containing sorbitol as a different saccharide.
Figure 6:
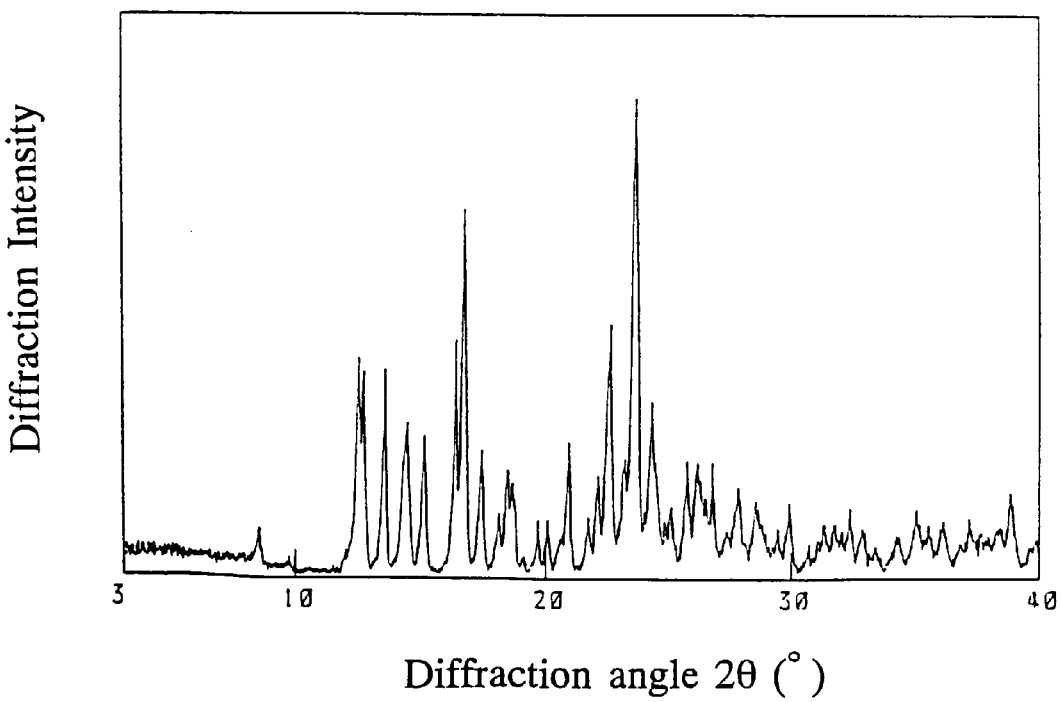
FIG. 6 is a powder x-ray diffraction pattern of trehalose containing maltitol as a different saccharide.

| Different saccharides | Crystallinity (%) | Powder x-ray diffraction pattern | Weight increased (%) | Fluidity | Solidification |
|---|---|---|---|---|---|
| None | 70 | FIG. 1 | 0.1 | Passable | Not found |
| Glucose | 68 | FIG. 2 | 0.1 | Passable | Not found |
| Maltose | 64 | FIG. 3 | 0.1 | Passable | Not found |
| Isomaltose | 26 | FIG. 4 | 8.8 | Impassable | Found |
| Maltotriose | 23 | — | 8.1 | Impassable | Found |
| Maltotetraose | 21 | — | 6.5 | Impassable | Found |
| Sorbitol | 68 | FIG. 5 | 0.2 | Passable | Not found |
| Maltitol | 65 | FIG. 6 | 0.2 | Passable | Not found |
| Isomaltitol | 22 | — | 7.0 | Impassable | Found |
| Maltotriitol | 24 | — | 8.2 | Impassable | Found |
| Maltotetraitol | 21 | — | 7.1 | Impassable | Found |

As evident from the results in Table 1, it was revealed that glucose, maltose, sorbitol, and maltitol unexpectedly crystallized along with trehalose in the presence of trehalose to give a relatively-highly increased crystallinity. Among the powder x-ray diffraction patterns, as compared with FIG. 1 for a powder x-ray diffraction pattern of crystalline trehalose hydrate as a control, FIGS. 2, 3, 5 and 6 show the patterns for crystalline glucose hydrate, crystalline maltose hydrate, crystalline sorbitol anhydride, and crystalline maltitol anhydride, respectively, as well as showing that for crystalline trehalose hydrate. The data shows that these crystalline saccharides had crystallized along with trehalose in the presence of trehalose. It was also found that the powdery saccharides, formed as a result of the crystallization of these saccharides along with trehalose in the presence of trehalose, had a satisfactory stability, relatively-high crystallinity, relatively-low hygroscopicity, insubstantial solidification, and satisfactory fluidity. The saccharides, which did not crystallize along with trehalose, were isomaltose, maltotriose, maltotetraose, isomaltitol, maltotruitol, and maltotetraitol. In the aqueous trehalose solutions containing these saccharides, only trehalose crystallized, resulting in a relatively-low crystallinity as a whole, and a similar powder x-ray diffraction pattern. Because of this, FIG. 4 with isomaltose was shown as a representative of the crystallized saccharides.

Experiment 2

Influence of crystallinity on the property of powdery saccharide containing trehalose and different saccharide The influence of crystallinity on the property of powdery saccharides, containing trehalose and a different saccharide, was studied. In accordance with the method in Experiment 1, an about 85% aqueous solution containing the trehalose and a different saccharide(s) of glucose and/or maltose, d.s.b., was prepared, and mixed with 0.2% of respective crystalline trehalose hydrate, crystalline glucose hydrate, and/or crystalline maltose hydrate as seeds to the total saccharides, d.s.b. The mixture was kneaded and allowed to stand at 25° C. while being sampled at prescribed time intervals. The samples were dried in vacuo at 40° C. for 16 hours and pulverized into powdery saccharides. In accordance with the method in Experiment 1, the powdery saccharides were analyzed for crystallinity on powder x-ray diffraction analysis, and observed whether they had a passable fluidity or not and whether they solidified or not by allowing them to stand at a relative humidity of 90% and at 25° C. for four days based on the determination of the degree of hygroscopicity or the weight increased. The results were in Table 2:

TABLE 2

| Different saccharides | Standing time (hour) | Crystallinity (%) | Weight increased (%) | Fluidity | Solidification |
|---|---|---|---|---|---|
| Glucose | 3 | 13 | 5.6 | Impassable | Found |
|  | 6 | 19 | 5.0 | Impassable | Found |
|  | 12 | 35 | 2.7 | Passable | Not found |
|  | 20 | 42 | 0.3 | Satisfactory | Not found |
|  | 40 | 50 | 0.2 | Satisfactory | Not found |
|  | 72 | 60 | 0.1 | Satisfactory | Not found |
|  | 96 | 66 | 0.1 | Satisfactory | Not found |
| Maltose | 3 | 11 | 5.8 | Impassable | Found |
|  | 6 | 17 | 5.1 | Impassable | Found |
|  | 12 | 32 | 2.8 | Passable | Not found |
|  | 20 | 41 | 0.4 | Satisfactory | Not found |
|  | 40 | 49 | 0.2 | Satisfactory | Not found |
|  | 72 | 58 | 0.1 | Satisfactory | Not found |
|  | 96 | 62 | 0.1 | Satisfactory | Not found |
| Glucose + Maltose | 3 | 8 | 6.0 | Impassable | Found |
|  | 6 | 14 | 5.3 | Impassable | Found |
|  | 12 | 30 | 2.9 | Passable | Not found |
|  | 20 | 40 | 0.4 | Satisfactory | Not found |
|  | 40 | 48 | 0.1 | Satisfactory | Not found |
|  | 72 | 53 | 0.1 | Satisfactory | Not found |
|  | 96 | 60 | 0.1 | Satisfactory | Not found |

As evident from the results in Table 2, it was revealed that the powdery saccharides containing trehalose and a different saccharide(s) were relatively low in hygroscopicity to show a satisfactory fluidity when they had a crystallinity of about 30% or more, and the hygroscopicity was more reduced when the crystallinity was 40% or more, causing to show a satisfactory fluidity and stability free of solidification.

Experiment 3

Acute toxicity test

Crystalline powdery saccharides, obtained by the methods in the later described Examples A-1 to A-6, were tested in mice for acute toxicity test by administering orally. As a result, all of the saccharide gave a relatively-low toxicity, and no mouse died even when administered with a maximum possible dose. The data indicates that the $LD_{50}$ of the saccharides are 50 g/kg mouse weight or more.

The following Examples A and B explain the process for producing the crystalline powdery saccharides and the compositions containing thereof according to the present invention:

EXAMPLE A-1

To a 30% corn-starch suspension was added calcium carbonate to give a final concentration of 0.1%, and the mixture was adjusted to give a pH of 6.5, mixed with 0.2%/g starch of "TERMAMYL", an α-amylase specimen commercialized by Novo Industri A/S Copenhagen, Denmark, and enzymatically reacted at 95° C. for 15 min. The reaction mixture was heated by autoclaving at 120° C. for 10 min, cooled to 55° C., mixed with five units/g starch of a maltotetraose-forming amylase commercialized by Hayashibara Biochemical Laboratories Inc., Okayama, Japan, as disclosed in Japanese Patent Kokai No. 240,784/88, enzymatically reacted for six hours, further mixed with 30 units/g starch of "α-AMYLASE 2A", an α-amylase specimen commercialized by Hankyu Bioindustry Co., Ltd., Osaka, Japan, and enzymatically reacted at 65° C. for four hours. The reaction mixture was heated by autoclaving at 120° C. for 10 min, cooled to 45° C., mixed with two units/g starch of a non-reducing saccharide-forming enzyme as disclosed in Japanese Patent Kokai No.213,283/95, and enzymatically reacted for 64 hours. Thereafter, the reaction mixture was kept at 100° C. for 10 min to inactivate the remaining enzyme, then diluted up to give a concentration of about 20%. The dilute was mixed with 10 units/g starch of "GLUCOZYME", a glucoamylase specimen commercialized by Nagase Biochemicals, Ltd., Kyoto, Japan, and enzymatically reacted at 50° C. for 40 hours to obtain a reaction mixture containing about 25% trehalose with respect to the total saccharides, d.s.b. The reaction mixture was heated to inactivate the remaining enzyme and, in a conventional manner, decolored and filtered with activated charcoals and desalted with ion-exchange resins in H- and OH-form to obtain a purified saccharide solution, followed by concentrating the solution in vacuo to give a concentration of about 75%. The concentrate was placed in a crystallizer, admixed with about one percent of respective crystalline trehalose hydrate and crystalline glucose hydrate as seeds, and cooled gradually into a massecuite with a crystallinity of about 25%. The massecuite was spray dried and aged to obtain a crystalline powdery saccharide in a yield of about 90% to the material starch, d.s.b. The product is a stable powdery saccharide, which contains about 25% trehalose, about 72% glucose, and about 3% different saccharides, d.s.b., and has a crystallinity of about 66%, relatively-low hygroscopicity, and satisfactory fluidity. Because of these properties, the product can be arbitrarily used in food products, cosmetics, and pharmaceuticals as a sweetener, taste-improving agent, quality-improving agent, stabilizer, filler, excipient, or diluent.

EXAMPLE A-2

To a 10% potato starch suspension was added two units/g starch of "SPITASE HS", an α-amylase specimen commercialized by Nagase Biochemicals, Ltd., Kyoto, Japan, and the mixture was gelatinized and liquefied by heating under stirring conditions, then promptly heated by autoclaving at 120° C. for 10 min, and adjusted to 50° C. and pH 5.0. The resulting mixture was mixed with 20 units/g starch of a β-amylase specimen commercialized by Nagase Biochemicals, Ltd., Kyoto, Japan, and 500 units/g starch of an isoamylase specimen commercialized by Hayashibara Biochemical Laboratories Inc., Okayama, Japan, and enzymatically reacted for 24 hours to obtain a reaction mixture containing about 92% maltose to the total saccharides, d.s.b. The reaction mixture was kept at 100° C. for 20 min, cooled, adjusted to 10° C. and pH 7.0, then mixed with about one unit/g maltose of a maltose/trehalose converting enzyme as disclosed in Japanese Patent Kokai No. 170,977/95, and enzymatically reacted for 96 hours to obtain a reaction mixture containing about 69% trehalose to the total saccharides, d.s.b. The reaction mixture thus obtained was heated to inactivate the remaining enzyme and, in accordance with the method in Example A-1, decolored, and desalted into a purified saccharide solution, followed by the concentration in vacuo to give a concentration of about 85%. The concentrate was placed in a crystallizer, mixed with about one percent of respective crystalline trehalose hydrate and crystalline maltose hydrate as seeds, and kneaded into a massecuite which was then placed in a vat, allowed to stand at 20° C. for five days under a relative humidity of about 60% to crystallize and solidify the contents. The solid was pulverized by a cutter to obtain a crystalline powdery saccharide in a yield of about 90% to the material starch, d.s.b. The product is a stable powdery saccharide, which contains about 69% trehalose, about 23% maltose, and about 8% different saccharides, d.s.b., and has a crystallinity of about 58%, relatively-low hygroscopicity, and satisfactory fluidity. Because of these properties, the product can be arbitrarily used in food products, cosmetics, and pharmaceuticals as a sweetener, taste-improving agent, quality-improving agent, stabilizer, filler, excipient, or diluent.

EXAMPLE A-3

A reaction mixture, containing about 69% trehalose to the total saccharides, d.s.b., obtained by the method in Example A-2, was mixed with five units/g dry solids of glucoamylase, enzymatically reacted at 50° C. for 40 hours, and heated to inactivate the remaining enzyme. In accordance with the method in Example A-1, the reaction mixture was decolored and desalted into a purified saccharide solution which was then concentrated in vacuo to give a concentration of about 70%. The concentrate was placed in a crystallizer, mixed with about one percent of crystalline trehalose hydrate as a seed, crystallized under cooling conditions, and separated by centrifugation into a mother liquor and a high-purity crystalline trehalose hydrate. The mother liquor was concentrated in vacuo to give a concentration of about 85%, and the concentrate was placed in a crystallizer, mixed with about one percent of respective crystalline trehalose hydrate and crystalline glucose hydrate as seeds, and kneaded into a massecuite which was then placed in a vat, and allowed to stand at 25° C. for four days under a relative humidity of about 60% to crystallize and solidify the contents. Thereafter, the solid was pulverized by a cutter to obtain a crystalline powdery saccharide in a yield of about 95% to the material mother liquor, d.s.b. The product is a stable powdery saccharide, which contains about 60% trehalose, about 35% glucose, and about 5% different saccharides, d.s.b., and has a crystallinity of about 64%, relatively-low hygroscopicity, and satisfactory fluidity. Because of these properties, the product can be arbitrarily used in food products, cosmetics, and pharmaceuticals as a sweetener, taste-improving agent, quality-improving agent, stabilizer, filler, excipient, or diluent.

EXAMPLE A-4

*Thermus aquaticus,* ATCC 33923, which produces a maltose/trehalose converting enzyme, was cultured by the method as disclosed in Japanese Patent Kokai No. 170,977/ 95, and the culture was centrifuged to obtain 250 g wet cells with a total enzyme activity of about 7,500 units. Using sodium alginate solution and calcium chloride solution, the cells were immobilized. The cells immobilized with alginic acid were injected to a jacketed glass column, 5.4 cm diameter and 100 cm length, and kept at 60° C. A 40% maltose solution (pH 6.5) was fed to the column at an SV (space velocity) 0.2 by descending method to obtain a reaction mixture containing about 66% trehalose, about 28% maltose, and about 6% glucose, d.s.b. In accordance with the method in Example A-1, the mixture was decolored and desalted for purification, and concentrated in vacuo to give a concentration of about 75%. Thereafter, the concentrate was placed in a crystallizer, mixed with about one percent of respective crystalline trehalose hydrate and crystalline maltose hydrate as seeds, and gradually cooled to obtain a massecuite with a crystallinity of 25%. Similarly as in Example A-1, the massecuite was sprayed dried and aged to obtain a crystalline powdery saccharide in a yield of about 92% to the material maltose, d.s.b. The product is a stable powdery saccharide, which contains about 66% trehalose, about 28% glucose, and about 6% different saccharides, d.s.b., and has a crystallinity of about 60%, relatively-low hygroscopicity, and satisfactory fluidity. Because of these properties, the product can be arbitrarily used in food products, cosmetics, and pharmaceuticals as a sweetener, taste-improving agent, quality-improving agent, stabilizer, filler, excipient, or diluent.

EXAMPLE A-5

A mother liquor, obtained by the method in Example A-3, was adjusted to give a concentration of about 50%, and the solution was placed in an autoclave, admixed with 10% of the Raney nickel, heated up to give a temperature of 90–120° C. under stirring conditions, and hydrogenated by increasing the hydrogen pressure to a level of 20–120 kg/cm$^2$ to complete the hydrogenation. Thereafter, the Raney nickel was removed from the reaction system, and the resulting mixture was decolored and desalted for purification, and concentrated in vacuo into an about 75% solution. The solution was placed in a crystallizer, admixed with about two percent of respective crystalline trehalose hydrate and crystalline sorbitol anhydride as seeds, gradually cooled into a massecuite with a crystallinity of about 30%. The massecuite was spray dried and aged to obtain a crystalline powdered saccharide in a yield of about 95% to the material mother liquor, d.s.b. The product is a stable powdery saccharide, which contains about 60% trehalose, about 35% sorbitol, and about 5% different saccharides, d.s.b., and has a crystallinity of about 60%, relatively-low hygroscopicity, and satisfactory fluidity. Because of these properties, the product can be arbitrarily used in food products, cosmetics, and pharmaceuticals as a sweetener, taste-improving agent, quality-improving agent, stabilizer, filler, excipient, or diluent.

EXAMPLE A-6

The purified saccharide solution in Example A-4, obtained by decoloring and desalting in accordance with the method in Example A-1, was concentrated into an about 50% solution. In accordance with the method in Example A-5, the concentrate was hydrogenated, purified, and concentrated in vacuo to give a concentration of about 85%. The concentrate was placed in a crystallizer, admixed with about one percent of respective crystalline trehalose hydrate and crystalline maltitol anhydride as seeds, and kneaded into a massecuite which was then placed in a vat, and allowed to stand at 25° C. for five days under a relative humidity of about 50% to crystallize and solidify the contents. The solid was pulverized by a cutter to obtain a crystalline powdery saccharide in a yield of about 95% to the material purified saccharide solution, d.s.b. The product, which contains about 66% trehalose, about 28% maltitol, and about 6% sorbitol, d.s.b., and has a crystallinity of about 60%, relatively-low hygroscopicity, and satisfactory fluidity. Because of these properties, the product can be arbitrarily used in food products, cosmetics, and pharmaceuticals as a sweetener, taste-improving agent, quality-improving agent, stabilizer, filler, excipient, or diluent.

EXAMPLE B-1

Sweetener

A powdery mixed sweetener was obtained by mixing to homogeneity four parts by weight of sucrose with six parts by weight of a crystalline powdery saccharide obtained by the method in Example A-6. The product is a relatively-low-caries-inducing sweetener with a satisfactory sweetness.

EXAMPLE B-2

Sweetener

One part by weight of a crystalline powdery saccharide, obtained by the method in Example A-5, was mixed to homogeneity with 0.01 part by weight of "αG SWEET", an α-glycosyl stevioside product commercialized by Toyo Sugar Refining Co., Ltd., Tokyo, Japan, and 0.01 part by weight of "ASPARTAME", L-phenylalanine methyl ester, commercialized by Ajinomoto Co. Ltd., Tokyo, Japan, and the mixture was fed to a granulator into a granule of sweetener. The product has a satisfactory quality of sweetness, an about two-fold higher sweetening powder of sucrose, and an about half calorific-value of sucrose with respect to the sweetening power. The sweetener has a satisfactory stability and has substantially no fear of decomposing the mixed sweeteners with a high sweetening power, and it can be suitably used as a low-caloric sweetener to sweeten low-caloric food products for fat persons and diabetics who are restricted to take unnecessary calories. Since the sweetener less forms acids and insoluble glucans by dental-caries-inducing microorganisms, it can be advantageously used to sweeten dental-caries-inhibitory food products.

EXAMPLE B-3

Cream Wafer

Two thousand parts by weight of a crystalline powdery saccharide obtained by the method in Example A-1, 1,000 parts by weight of a shortening, one part by weight of lecithin, one part by weight of lemon oil, and an adequate amount of vanilla oil were mixed in a conventional manner into a cream which was then heated to keep at temperatures of 40–50° C. and sandwiched with wafers to obtain a cream wafer. The product has a satisfactory taste and flavor.

EXAMPLE B-4

Custard Cream

Five hundred parts by weight of corn starch, 500 parts by weight of a crystalline powdery saccharide obtained by the method in Example A-2, 400 parts by weight of sucrose, and five parts by weight of salt, and the mixture was passed through a sieve for sufficient mixing, then admixed with 1,400 parts by weight of fresh eggs, and gradually mixed with 5,000 parts by weight of boiling milk. Then, the resulting mixture was continued stirring under gentle heating conditions, and the heating was stopped when the corn starch was completely gelatinized to show the whole contents semitransparent. The resulting mixture was cooled and mixed with a small amount of a vanilla flavor into a custard cream. The product has a smooth surface, mild sweetness, and satisfactory taste.

EXAMPLE B-5

Chocolate

Forty parts by weight of cacao paste, 10 parts by weight of cacao butter, and 50 parts by weight of a crystalline powdery saccharide obtained by the method in Example A-3 were mixed, and the mixture was passed through a refiner to reduce the granule size, placed in a conche, and kneaded up over two days and nights. During the kneading step, 0.5 part by weight of lecithin was added to the resulting mixture and sufficiently dispersed therein. Thereafter, the resulting mixture was adjusted to give a temperature of 31° C. by a thermo-controller, then poured into a mold just before the butter was solidified, deaerated by a vibrator, and solidified by passing through a cooling tunnel kept at 10° C. over 20 min, followed by removing the solidified contents from the mold and packaging the contents into the desired product. The product has substantially no hygroscopicity, but has a satisfactory color, gloss, and internal tissues, and it moderately melts in your mouth to give a high-quality sweetness and mild taste and flavor.

EXAMPLE B-6

Chewing Gum

Twenty-five parts by weight of a gum base and 40 parts by weight of a massecuite obtained by the method in Example A-6 were kneaded by a mixer at 60° C., and the mixture was admixed with 30 parts by weight of a crystalline powdery saccharide obtained by the method in Example A-5, 1.5 parts by weight of calcium phosphate, and 0.1 part by weight of an l-menthol-β-cyclodextrin inclusion compound, further admixed with a small amount of a seasoning. The resulting mixture was sufficiently kneaded and rolled into the desired product. The product is a relatively-low-caries-inducing chewing gum.

EXAMPLE B-7

Instant Juice

To 33 parts by weight of an orange juice powder obtained by spray drying were added 60 parts by weight of a crystalline powdery saccharide obtained by the method in Example A-1, 0.6 part by weight of citric acid anhydride, 0.1 part by weight of malic acid, 0.1 part by weight of L-ascorbic acid, 0.1 part by weight of sodium citrate, 0.6 part by weight of a powdery flavor, and 0.5 part by weight of pullulan, and the mixture was sufficiently mixed, and the mixture was subjected to a fluidized-bed granulator, which had been set to a blowing air temperature of 40° C. and an airflow of 150 m$^3$, sprayed with a trehalose-enriched saccharide concentrate obtained by the method in Example A-2, as a coating solution or a binder, at a spraying-rate of 100 ml/min, and granulated for 30 min into an instant juice containing 30% orange juice. The product is free from unsatisfactory taste and flavor and is stable for a relatively-long period of time without absorbing moisture and solidifying.

EXAMPLE B-8

Uiro-no-moto (Premix for Uiro)

Ninety parts by weight of rice powder was mixed to homogeneity with 20 parts by weight of corn starch, 120 parts by weight of a crystalline powdery saccharide obtained by the method in Example A-2, and four parts by weight of pullulan to obtain an uiro-no-moto. Two hundred parts by weight of the premix and one gram of a matcha (a powdered tea) were added to water and sufficiently mixed. The mixture was placed in a container and steamed for 60 min to obtain a matcha uiro (a starch paste with matcha). The product has a satisfactory gloss, biting property, taste, and flavor, and has a relatively-long shelf-life because the retrogradation of the starch is well prevented.

EXAMPLE B-9

Bettara-zuke-no-moto (A Premix for Fresh Radish Pickles)

Four parts by weight of a crystalline powdery saccharide obtained by the method in Example A-5, 0.05 part by weight of a licorice preparation, 0.008 part by weight of malic acid, 0.07 part by weight of sodium glutamate, 0.03 part by weight of potassium sorbate, and 0.2 part by weight of pullulan were mixed to homogeneity to obtain a bettara-zuke-no-moto. Thirty kilograms of fresh radishes were first pickled with salt in a conventional manner, then pickled with sugar and soaked in a seasoning solution, prepared with four kilograms of the premix, to obtain a bettara-zuke (fresh radish pickles). The product has a satisfactory color, gloss, and flavor, and has an adequate sweetness and biting property. The product is substantially free of acidification and is stable for a relatively-long period of time.

EXAMPLE B-10

Beverage with Lactic Acid Bacteria

One hundred and seventy-five parts by weight of skim milk, 80 parts by weight of a crystalline powdery saccharide obtained by the method in Example A-3, and 50 parts by weight of a lactosucrose enriched powder as disclosed in Japanese Patent Kokai No. 281,795/92 were dissolved in 1,200 parts by weight of water, and the solution was sterilized by incubating at 65° C. for 30 min, and cooled to 40° C. Thereafter, 30 parts by weight of a lactic acid bacterium as a starter was inoculated to the above solution and incubated at 37° C. for eight hours to obtain a beverage with lactic acid bacteria with a satisfactory taste and flavor. Since the product contains oligosaccharides, it stably retains the bacteria and promotes the growth of bifid bacteria in the intestines.

EXAMPLE B-11

Bread

One hundred parts by weight of wheat flour, two parts by weight of yeast, five parts by weight of sugar, one part by weight of a crystalline powdery saccharide obtained by the method in Example A-2. and 0.1 part by weight of a yeast food were kneaded with water in a conventional manner. The mixture was allowed to ferment at 26° C. for two hours, aged for 30 min, and backed up. The product is a relatively-high quality bread having a satisfactory color, texture, adequate elasticity, and mild sweetness.

EXAMPLE B-12

Ham

In 1,000 parts by weight of hams were rubbed to homogeneity 15 parts by weight of salt and three parts by weight of potassium nitrate, and the hams were piled up and allowed to stand in a cool room overnight, followed by soaking them for a week in a salt solution for pickling, consisting of 500 parts by weight of water, 100 parts by weight of salt, three parts by weight of potassium nitrate, 40 parts by weight of a crystalline powdery saccharide obtained by the method in Example A-5, and an adequate amount of a spice. The resulting hams were in a conventional manner washed with cool water, tied up with a string, smoked, cooked, cooled, and packed into the desired product. The product is a high-quality ham with a satisfactory color, taste, and flavor.

EXAMPLE B-13

Cosmetic Cream

Two parts by weight of polyoxyethylene glycol monostearate, five parts by weight of self-emulsifying glycerine monostearate, two parts by weight of a crystalline powdery saccharide obtained by the method in Example A-6, one part by weight of α-glycosyl rutin, one part by weight of liquid paraffin, 10 parts by weight of glycerol trioctanate, and an adequate amount of an antiseptic were mixed. The mixture was dissolved by heating in a conventional manner, mixed with two parts by weight of L-lactic acid, five parts by weight of 1,3-butylene glycol, and 66 parts by weight of refined water, emulsified by a homogenizer, and further mixed with an appropriate amount of a flavor into a cosmetic cream. The product has an antioxidation activity and a relatively-high stability, and can be arbitrarily used as a sunscreen, skin-refining agent, and skin-whitening agent.

EXAMPLE B-14

Toothpaste

| Ingredients | Percent (%) |
|---|---|
| Dicalcium hydrogenphosphate | 45.0 |
| Pullulan | 2.95 |
| Sodium lauryl sulfate | 1.5 |
| Glycerine | 20.0 |
| Polyoxyethylene sorbitan laurate | 0.5 |
| Antiseptic | 0.05 |
| A crystalline powdery saccharide obtained by the method in Example A-5 | 12.0 |
| Maltitol | 5.0 |
| Water | 13.0 |

The ingredients were mixed in a conventional manner into a toothpaste which has a moderate sweetness and a favorable applicability for children.

EXAMPLE B-15

Sugar Coated Tablet

A crude tablet as a core, 150 mg weight, was coated with a first solution consisting of 40 parts by weight of a crystalline powdery saccharide obtained by the method in Example A-4, two parts by weight of pullulan having an average molecular weight of 200,000, 30 parts by weight of water, 25 parts by weight of talc, and three parts by weight of titanium oxide until reaching to about 230 mg. The resulting tablet was further coated with a second solution consisting of 65 parts by weight of a fresh preparation of the same crystalline powdery saccharide, one part by weight of pullulan, and 34 parts by weight of water, and further glossed with a liquid wax into a sugar coated tablet having a satisfactory gloss and appearance. The product has a satisfactory shock tolerance and relatively-long shelf-life without losing the high quality.

EXAMPLE B-16

Ointment for Trauma

Two hundred parts by weight of a crystalline powdery saccharide obtained by the method in Example A-4, and 300 parts by weight of maltose were mixed with 50 parts by weight of methanol dissolving three parts by weight of iodine, and further mixed with 200 parts by weight of a 10 w/v % aqueous pullulan solution to obtain an ointment for trauma with an adequate extensibility and adhesiveness. The product has a germicidal activity due to the iodine and acts as an agent for supplementing energy to the tissues due to the trehalose and maltose, and this shortens the healing period and satisfactorily cures wounded sites.

As evident from the above, the present crystalline powdery saccharide is one which contains crystals of trehalose and a different saccharide(s), obtained by crystallizing the trehalose along with the different saccharide(s) crystallizable in the presence of trehalose, preferably, a crystalline powdery saccharide having a crystallinity of 40% or more, less hygroscopicity, and satisfactory fluidity and handleability. Such an establishment resulted in the outstanding improvement of the product value of powdery saccharides containing trehalose and a different saccharide(s) and, as a contribution, it greatly influences on the sugar industries correlating to trehalose production using starch and/or maltose as materials, and has an industrial significance throughout food-, cosmetic-, pharmaceutical-, and agricultural/forestry/fishery-industries which can utilize the present crystalline powdery saccharide.

While there has been described what is at present considered to be the preferred embodiments of the invention, it will be understood the various modifications may be made therein, and it is intended to cover in the appended claims all such modifications as fall within the true spirits and scope of the invention.

We claim:

1. A crystalline powdery saccharide obtainable by crystallizing trehalose along with a different saccharide crystallizable in the presence of trehalose.

2. The saccharide of claim 1, wherein said different saccharide is one selected from the group consisting of glucose, maltose, sorbitol, and maltitol.

3. The saccharide of claim 1, wherein the proportion of said trehalose and said different saccharide is from 9:1 to 1:9, on a dry solid basis.

4. The saccharide of claim 1, which has a crystallinity of 40% or more on powder x-ray diffraction analysis.

5. A process for producing a crystalline powdery saccharide, comprising:
    (a) crystallizing trehalose along with a different saccharide crystallizable in the presence of trehalose in an aqueous solution containing said trehalose and said different saccharide;
    (b) pulverizing the crystallized saccharides; and
    (c) collecting the resulting crystalline powdery saccharide.

6. The process of claim 5, wherein said aqueous solution is prepared from an aqueous solution obtained by enzymatically treating an aqueous solution containing starch and/or maltose.

7. The process of claim 5, wherein said different saccharide is one selected from the group consisting of glucose, maltose, sorbitol, and maltitol.

8. The process of claim 5, wherein the proportion of said trehalose and said different saccharide is from 9:1 to 1:9, on a dry solid basis.

9. The process of claim 5, wherein the crystallization step is effected by coexisting seeds of said trehalose and said different saccharide in said aqueous solution.

10. The process of claim 5, wherein the crystallization and pulverization steps are selected from the group consisting of spray drying, fluidized-bed granulation, and block pulverization.

11. The process of claim 10, wherein the spray drying comprises spraying from a nozzle a 65–80%, on a dry solid basis, of massecuite containing trehalose and a different saccharide(s) crystallizable in the presence of trehalose, and having a crystallinity of 5–30%; drying the sprayed contents with air heated to 60–90° C.; and crystallizing and ageing the dried contents while air heated to 30–60° C. is blowing to the contents for about 1–24 hours.

12. The process of claim 10, wherein said fluidized-bed granulation comprises concentrating by heating a solution containing trehalose along with a different saccharide(s) crystallizable in the presence of trehalose into a supersaturated solution with a concentration of 90% or more; mixing the supersaturated solution with a seed of the trehalose and different saccharide(s) in a hydrous and/or anhydrous form at a temperature below the melting points of the saccharides; pulverizing the resulting contents; and crystallizing and ageing the pulverized contents.

13. The process of claim 10, wherein said block-pulverization comprises placing in a container a 80–95%, on a dry solid basis, of massecuite containing trehalose along with a different saccharide(s) crystallizable in the presence of trehalose; allowing to stand the massecuite for about 1–20 days at ambient temperature to solidify and crystallize the contents into a block; and pulverizing and drying the block.

14. The process of claim 5, wherein said crystalline powdery saccharide has a crystallinity of 40% or more, on powder x-ray diffraction analysis.

* * * * *